(12) United States Patent
Sakami et al.

(10) Patent No.: US 9,452,963 B2
(45) Date of Patent: Sep. 27, 2016

(54) METHOD FOR PRODUCING 1,3-BUTADIENE AND/OR 3-BUTEN-2-OL

(71) Applicants: TORAY INDUSTRIES, INC., Tokyo (JP); NATIONAL UNIVERSITY CORPORATION CHIBA UNIVERSITY, Chiba-Shi, Chiba (JP)

(72) Inventors: Satoshi Sakami, Kamakura (JP); Katsushige Yamada, Kamakura (JP); Satoshi Sato, Chiba (JP); Hailing Duan, Chiba (JP)

(73) Assignee: TORAY INDUSTRIES, INC., Chiba (JP)

( * ) Notice: Subject to any disclaimer, the term of this patent is extended or adjusted under 35 U.S.C. 154(b) by 0 days.

(21) Appl. No.: 14/917,779

(22) PCT Filed: Sep. 8, 2014

(86) PCT No.: PCT/JP2014/073648
§ 371 (c)(1),
(2) Date: Mar. 9, 2016

(87) PCT Pub. No.: WO2015/037556
PCT Pub. Date: Mar. 19, 2015

(65) Prior Publication Data
US 2016/0221904 A1 Aug. 4, 2016

(30) Foreign Application Priority Data

Sep. 9, 2013 (JP) .................................. 2013-186946

(51) Int. Cl.
*C07C 27/00* (2006.01)
*C07C 29/60* (2006.01)
*C07C 1/24* (2006.01)

(52) U.S. Cl.
CPC .................. *C07C 29/60* (2013.01); *C07C 1/24* (2013.01); *C07C 2523/10* (2013.01)

(58) Field of Classification Search
CPC .......... C07C 29/60; C07C 33/03; C07C 1/24; C07C 11/167; C07C 2523/10
USPC .................................. 568/903; 585/327, 607
See application file for complete search history.

(56) References Cited

U.S. PATENT DOCUMENTS

| 2,527,120 | A | 10/1950 | Denivelle |
| 2011/0143406 | A1 | 6/2011 | Moriyama |
| 2014/0238841 | A1 | 8/2014 | Kawamura |
| 2015/0361007 | A1 | 12/2015 | Millet |

FOREIGN PATENT DOCUMENTS

| JP | 63222135 | 9/1988 |
| JP | 2010047505 | 3/2010 |
| JP | 2010150248 | 7/2010 |
| JP | 2014172883 | 9/2014 |
| KR | 1020120096125 | 8/2012 |
| KR | 1020120099818 | 9/2012 |
| KR | 1020120107353 | 10/2012 |
| WO | 2007094178 | 8/2007 |
| WO | 2009151342 | 12/2009 |
| WO | 2014118484 | 8/2014 |
| WO | 2013054874 | 3/2015 |

OTHER PUBLICATIONS

Aebi, J., et al., "Synthesis, conformation, and immunosuppressive activities of three analogs of cyclosporin A modified in the 1-position," 1990, pp. 999-1009, vol. 33(3), Journal of Medicinal Chemistry (abstract only).
Bos, M., et al., "Novel agonists of 5HT2C receptors. Synthesis and biological evaluation of substituted 2-(Indol-1-yl)-1-methylethylamines and 2-(Indeno[1,2-b] pyrrol-1-yl)-1-methylethylamines. Improved therapeutics for obsessive compulsive disorder," 1997, pp. 2762-2769, vol. 40(17), Journal of Medicinal Chemistry (abstract only).
Celinska, E., et al., "Biotechnological production of 2,3-butanediol—current state and prospects," Nov.-Dec. 2009, pp. 715-725, vol. 27(6), Biotechnology Advances (abstract only).
Duan, H., et al., "Dehydration of 2,3-butanediol into 3-buten-2-ol catalyzed by ZrO2," Mar. 10, 2014, pp. 1-4, vol. 48, Catalysis Communications (abstract only).
Ichikawa, N., et al., "Catalytic reaction of 1,3-butanediol over solid acids," Aug. 18, 2006, pp. 106-112, vol. 256, Issues 1-2, Journal of Molecular Catalysis A: Chemical (abstract only).
International Search Report for International Application No. PCT/JP2014/073648 mailed Oct. 28, 2014.
Li, ZJ., et al., "Microbial production of meso-2,3-butanediol by metabolically engineered *Escherichia coli* under low oxygen condition," Aug. 2010, pp. 2001-2009, vol. 87(6), Applied Microbiology and Biotechnology (abstract only).
Lundeen, A. et al., "Selective catalytic dehydration. Thoria-catalyzed dehydration of alcohols," 1967, pp. 3386-3389, vol. 32(11), The Journal of Organic Chemistry (abstract only).
Sato, F., "Dehydration of 1,5-pentanediol over rare earth oxides," Feb. 2012, pp. 41-48, vol. 419-420, Applied Catalysis A: General (abstract only).
Sato, S., et al., "Dehydration of diols catalyzed by CeO2," Nov. 2004, pp. 177-183, vol. 221, Issues 1-2, Journal of Molecular Catalysis A: Chemical (abstract only).
Written Opinion of the International Searching Authority for International Application No. PCT/JP2014/073648 mailed Oct. 28, 2014.

*Primary Examiner* — Jafar Parsa
(74) *Attorney, Agent, or Firm* — RatnerPrestia (57) ABSTRACT

Disclosed is a method for producing 1,3-butadiene and/or 3-buten-2-ol from 2,3-butanediol with high selectivity without using a radioactive substance. The method for producing 1,3-butadiene and/or 3-buten-2-ol comprises the step of dehydrating 2,3-butanediol in the presence of scandium oxide. The method enables the production of 1,3-butadiene and/or 3-buten-2-ol from 2,3-butanediol with high selectivity without using a radioactive substance.

4 Claims, 1 Drawing Sheet

METHOD FOR PRODUCING 1,3-BUTADIENE AND/OR 3-BUTEN-2-OL

CROSS-REFERENCE TO RELATED APPLICATIONS

This is the U.S. National Phase application of PCT International Application No. PCT/JP2014/073648, filed Sep. 8, 2014, and claims priority to Japanese Patent Application No. 2013-186946, filed Sep. 10, 2013, the disclosures of each of these applications being incorporated herein by reference in their entireties for all purposes.

FIELD OF THE INVENTION

The present invention relates to a method for producing 1,3-butadiene and/or 3-buten-2-ol by using a biomass resource-derived substance as a raw material.

BACKGROUND OF THE INVENTION 1,3-Butadiene is a highly important key substance in the chemical industry that has been used as a raw material for various chemical products. Chemical products including synthetic rubbers such as styrene-butadiene rubbers, polybutadiene rubbers, and chloroprene rubbers, as well as ABS resins, adiponitrile and 1,4-butanediol have been produced by using 1,3-butadiene as a raw material. As industrial methods for producing 1,3-butadiene, a production method by separating 1,3-butadiene from B-B fraction (a mixture containing C4 olefins mainly) generated by carrying out naphtha cracking, a production method by dehydrogenating butane or butene, or the like has been known (Non Patent Document 1).

3-Buten-2-ol is a useful substance that can be converted to 1,3-butadiene by dehydration. Examples of a method for converting 3-buten-2-ol to 1,3-butadiene include a method for dehydrating 3-buten-2-ol in the presence of silica-alumina catalyst as disclosed in Non Patent Document 2. 3-Buten-2-ol is a useful substance that can be converted to 1,3-butadiene and can be used as a raw material of pharmaceuticals or the like (Non Patent Document 3, Non Patent Document 4). As methods for producing 3-buten-2-ol, Non Patent Document 5 discloses a production method by reacting methylmagnesium iodide with acrolein, and a production method by partially oxidizing 2-butanol; and Patent Document 1 discloses a production method by reducing methyl vinyl ketone.

On the other hand, in recent years, the problem of global warming caused by greenhouse gases such as carbon dioxide generated from fossil resources, or the problem of depletion of fossil resources is growing into a serious problem. Owing to this, necessities for preventing the global warming and shifting to sustainable recycling-oriented society are increasing. In chemical industries, it is an urgent task to construct techniques to produce various chemical products from substances derived from biomass resources which are renewable resources. Both the above-mentioned 1,3-butadiene and 3-buten-2-ol are produced by using fossil resources as raw materials, and it is therefore very important to shift the raw materials to biomass resources in view of global environmental protection and reduction of fossil resources.

Since 2,3-butanediol can be produced by microbial fermentation using sugars as a raw material, it is a substance derivable from biomass resources (Non-patent Document 6). Thus, if 2,3-butanediol can be converted to 1,3-butadiene and/or 3-buten-2-ol, the raw materials of 1,3-butadiene and/or 3-buten-2-ol can be then shifted to the biomass resources.

The reaction to convert 2,3-butanediol to 1,3-butadiene is a dehydration reaction to eliminate two water molecules from 2,3-butanediol, and the reaction to convert 2,3-butanediol to 3-buten-2-ol is a dehydration reaction to eliminate one water molecule from 2,3-butanediol. Although the dehydration reaction of 2,3-butanediol is known to proceed by using an acid catalyst, the main product is methyl ethyl ketone in many cases.

As methods for converting 2,3-butanediol to 1,3-butadiene, a conversion method by dehydration reaction using thorium oxide as a catalyst (Non-patent Document 7), a conversion method by dehydration reaction using cesium oxide-silica complex as a catalyst (Patent Document 2), a method for reacting 2,3-butanediol with acetic acid to obtain 2,3-diacetoxybutane, and then thermally decomposing and converting the obtained 2,3-diacetoxybutane to 1,3-butadiene (Non-patent Document 8), and the like are known.

As methods for converting 2,3-butanediol to 3-buten-2-ol, a conversion method by dehydration reaction using thorium oxide as a catalyst (Non-patent Document 7), and a conversion method by dehydration reaction using a catalyst containing hydroxyapatite (Non-patent Document 3) are known.

The reaction to dehydrate 2,3-butanediol to produce 3-buten-2-ol belongs to a reaction to dehydrate a secondary alcohol to produce 1-alkene. As an example of reactions to produce 1-alkene in preference to 2-alkene from a secondary alcohol, Non-patent Document 9 discloses a method to dehydrate 4-methyl-2-pentanol to produce 4-methyl-1-pentene selectively. As catalysts for promoting this reaction, scandium oxide, cerium oxide, ytterbium oxide, samarium oxide and the like are disclosed.

PRIOR ART DOCUMENTS

Patent Documents

[Patent Document 1] JP 63-222135 A
[Patent Document 2] KR 2012-0099818 A
[Patent Document 3] KR 2012-0107353 A Non-Patent Documents

[Non-patent Document 1] K. Weissermel and H.-J. Arpe, translation supervisor Teruaki Mukaiyama, "Industrial Organic Chemistry—Important Raw Materials and Intermediates—5th Edition", Tokyo Kagaku Dojin, issued on Dec. 16, 2004, p. 114-119.
[Non-patent Document 2] Journal of Molecular Catalysis A: Chemical, vol. 256, issue 1-2, p. 106-112 (2006).
[Non-patent Document 3] Journal of Medicinal Chemistry, vol. 40, issue 17, p. 2762-2769 (1997).
[Non-patent Document 4] Journal of Medicinal Chemistry, vol. 33, issue 3, p. 999-1009 (1990).
[Non-patent Document 5] Chemical Encyclopedia, vol. 9, issued by Kyoritsu Shuppan, 1962, p. 183.
[Non-patent Document 6] Biotechnology Advances, vol. 27, p. 715-725 (2009).
[Non-patent Document 7] Journal of the Council of Industrial Research, vol. 18, p. 412-423 (1945).
[Non-patent Document 8] Industrial and Engineering Chemistry, vol. 37, issue 9, p. 905-908 (1945).
[Non-patent Document 9] Journal of Organic Chemistry, vol. 32, issue 11, p. 3386-3389 (1967).

SUMMARY OF THE INVENTION

Problems to be Solved by the Invention

As described above, 2,3-butanediol can be derived from biomass resources and can be converted to 1,3-butadiene and/or 3-buten-2-ol through chemical conversion. However, as to the method for converting 2,3-butanediol to 1,3-butadiene and/or 3-buten-2-ol in the presence of thorium oxide as disclosed in Non-patent Document 7, since the thorium oxide is a radioactive substance, it is very difficult to apply this method to industrial production. The method for reacting 2,3-butanediol with acetic acid to obtain 2,3-diacetoxybutane, and then thermally decomposing and converting the obtained 2,3-diacetoxybutane to 1,3-butadiene as disclosed in Non-patent Document 8 has many steps and requires the recovery and reuse of acetic acid, which means a very complicated process. The method for converting 2,3-butanediol to 1,3-butadiene in the presence of cesium oxide-silica complex as disclosed in Patent Document 2 has also a drawback that the selectivity of 1,3-butadiene is low. Further, the method for converting 2,3-butanediol to 3-buten-2-ol by using a catalyst containing hydroxyapatite as disclosed in Patent Document 3 has a drawback that the selectivity of 3-buten-2-ol is quite low.

As an example of the methods for producing 1-alkene selectively from a secondary alcohol, Non-patent Document 9 discloses a method for dehydrating 4-methyl-2-pentanol to produce 4-methyl-1-pentene selectively. However, this method is not always applicable to dehydration reaction of 2,3-butanediol to produce 3-buten-2-ol. As will be shown in Comparative Examples 2 to 16, most of the catalysts for dehydrating 4-methyl-2-pentanol to produce 4-methyl-1-pentene selectively, as disclosed in Non-patent Document 9, could not be applied to the dehydration of 2,3-butanediol to produce 3-buten-2-ol.

As described above, although several methods for producing 1,3-butadiene and/or 3-buten-2-ol from 2,3-butanediol have been known, a production method with high selectivity without using a radioactive substance has been strongly demanded.

Means for Solving the Problems

As a result of intensive study to solve the above problem, the present inventors discovered a method for producing 1,3-butadiene and/or 3-buten-2-ol from 2,3-butanediol with high selectivity without using a radioactive substance, thereby completing the present invention.

That is, the present invention provides a method for producing 1,3-butadiene and/or 3-buten-2-ol, which method comprise the step of dehydrating 2,3-butanediol in the presence of scandium oxide.

In an embodiment of the present invention, the reaction temperature of the step of dehydrating 2,3-butanediol is not less than 270° C. and not more than 420° C.

In an embodiment of the present invention, the scandium oxide is one prepared by calcination at a temperature range of not less than 500° C. and not more than 1000° C.

In an embodiment of the present invention, the method further comprising the step of dehydrating 3-buten-2-ol produced in the step of dehydrating 2,3-butanediol in the presence of scandium oxide, in the presence of an acid catalyst to produce 1,3-butadiene.

The reaction to dehydrate 2,3-butanediol in the presence of scandium oxide to produce 1,3-butadiene and/or 3-buten-2-ol, which is an embodiment of the present invention, can be described by the reaction equation below.

The reaction to dehydrate 3-buten-2-ol in the presence of an acid catalyst to produce 1,3-butadiene, which is one aspect of the present invention, can be described by the reaction equation below:

Effect of the Invention

By the present invention, 1,3-butadiene and/or 3-buten-2-ol can be produced from 2,3-butanediol with high selectivity without using a radioactive substance.

MODE FOR CARRYING OUT THE INVENTION

In the present invention, "biomass resources" mean renewable organic resources derived from organisms, which are originated from organic matter produced by carbon dioxide fixation by plants using solar energy. Specific examples thereof include maize, sugarcane, tubers, wheat, rice, soybean, pulp, kenaf, rice straw, wheat straw, bagasse, corn stover, switchgrass, weed, woods, waste paper, charcoal, natural rubber, raw cotton, as well as animal and vegetable fats and oils such as safflower oil, sunflower oil, soybean oil, corn oil, rapeseed oil, olive oil, palm oil, castor oil, beef tallow, lard, fish oil, and whale oil.

In the present invention, the substance derived from biomass resources (biomass resource-derived substance) means a substance that is induced, that can be induced, or that was induced, from the above-described biomass resources by fermentation, chemical conversion or the like.

As 2,3-butanediol that is the raw material of the present invention, a biomass resources-derived one obtained by microbial fermentation is available as described in Non-patent Document 3. Examples of microorganisms capable of fermentation using sugars as carbon sources include *Klebsiella pneumoniae, Klebsiella* oxymora, and *Paenibacillus polymyxa*, which are naturally occurring microorganisms. These microorganisms can produce (2R,3R)-2,3-butanediol and meso-2,3-butanediol. As shown in WO 2007/094178, the genus *Ochrobactrum* is capable of selective production of (2S,3S)-2,3-butanediol. Further, as described in WO 2009/151342, *Clostridium autoethanogenum* is known to be a microorganism capable of fermentation using carbon monoxide as a carbon source. 2,3-Butanediol produced from such a microorganism is also included in the 2,3-butanediol in the present invention.

Alternatively, a method using a microorganism given a capacity to produce 2,3-butanediol by genetic recombination may be employed. Specific examples of such a method include the method described in "Applied Microbiolgy and Biotechnology, vol. 87, No. 6, pp. 2001-2009 (2010)".

The saccharides to be used in the fermentation to 2,3-butanediol by microorganism may be any saccharides including starch-derived glucose, cellulose-derived glucose, sucrose, molasses, glucose, galactose, xylose, fructose, arabinose and mannose, as long as the microorganism can use them. Glycerol may also be used for the fermentation to 2,3-butanediol. The 2,3-butanediol in the fermentation solution may be purified by using separation operations such as membrane separation, ion-exchange and/or distillation individually or in combination. For example, 2,3-butanediol with high purity may be isolated from fermentation solution by using methods disclosed in JP 2010-150248 A and WO 2013/054874.

As described above, 2,3-butanediol produced by microbial fermentation can be divided into three optical isomers, that is, (2R,3R)-2,3-butanediol, (2S,3S)-2,3-butanediol, and (2S,3R)-2,3-butanediol (meso-2,3-butanediol). The raw material of the present invention may be any of these isomers, or may be a mixture of a plurality of the isomers. The 2,3-butanediol may be a purified one or a crude one. Although the present invention is characterized in that the 2,3-butanediol available as a biomass resource-derived substance can be used as a raw material, 2,3-butanediol derived from fossil resources such as petroleum may also be used as the raw material.

The present invention include the step of dehydrating 2,3-butanediol, and in one embodiment of the present invention, the step of dehydrating 3-buten-2-ol is also included. These dehydration steps may be allowed to proceed with continuous reactors. The continuous reactor is a reactor in which a solid catalyst is packed in a tubular reactor and the raw material is allowed to pass through the catalyst layer to promote reaction. Specific examples of the packing types of the catalyst layer include the fixed bed in which the catalyst is left to stand, the moving bed in which the catalyst is moved, and the fluidized bed in which the catalyst is allowed to fluidize, but any type of these may be applied to the step of dehydrating 2,3-butanediol or 3-buten-2-ol.

Figure 1:
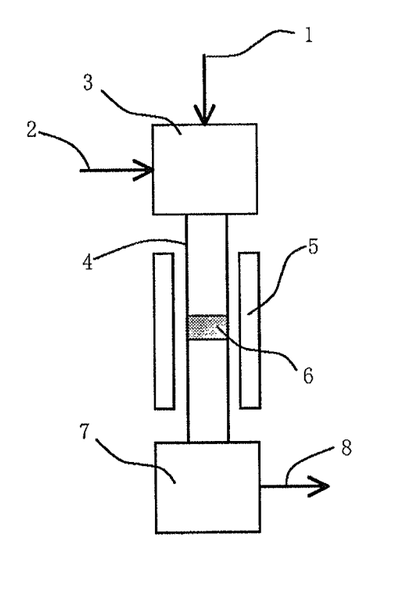
FIG. 1 is a schematic view illustrating one example of continuous reactors that can be used in the production method of the present invention.

The reactor to be used in the step of dehydrating 2,3-butanediol or 3-buten-2-ol is not limited, and for example, an apparatus exemplified in FIG. 1 may be used. The apparatus shown in FIG. 1 is constituted by a reaction tube 4, a raw material inlet 1, a vaporizer 3 provided with 2, reaction liquid collection container (condenser) 7 and tubular furnace 5, and the catalyst layer 6 may be fixed inside the reaction tube 4. The reaction tube 4 may be heated to a desired temperature with the tubular furnace 5. The gas-phase flow reaction using the apparatus of FIG. 1 may be carried out by feeding the raw material from the raw material inlet 1 to the vaporizer 3 and introducing the vaporized raw material into the reaction tube 4. The raw material may also be introduced to the reaction tube 4 together with carrier gas. The product may be collected as liquid in the reaction liquid collection container 7 or may be collected as gas from a gas vent 8.

In the step of dehydrating 2,3-butanediol or 3-buten-2-ol, the pressure inside the reactor is not limited. The pressure is preferably not less than 0.001 MPa and not more than 0.5 MPa. The dehydration may be easily carried out under atmospheric pressure at which no device or operation for reducing or increasing the pressure is necessary.

In the step of dehydrating 2,3-butanediol or 3-buten-2-ol, a carrier gas may be allowed to flow together with the reaction raw material inside the reactor. As the carrier gas, inert gases such as argon, helium and nitrogen, as well as hydrogen are preferably used. Although these gases may be used individually, a mixture of a plurality of the gases at an optional mixing ratio may also be used. For suppressing the decrease in activity of the catalyst used in the dehydration reaction, the carrier gas preferably contain hydrogen. Water vapor, air, oxygen and the like may also be contaminated in the carrier gas. The mixing ratio of the reaction raw material and the carrier gas may be selected properly. For example, the flow rate of the carrier gas may be from 20 mL/min. to 120 mL/min. per 1 g/hour of 2,3-butanediol or 3-buten-2-ol, but the flow rate is not limited thereto.

In the step of dehydrating 2,3-butanediol or 3-buten-2-ol, the contact time which is a physical quantity represented by W/F (hour) taking the feed rate of the reaction raw material as F (g/hour) and taking the catalyst weight as W (g), is not limited, but it is preferably not less than 0.01 hours and not more than 10 hours, and more preferably not less than 0.05 hours and mot more than 5 hours.

The present invention is characterized in that scandium oxide ($Sc_2O_3$) is used as a catalyst in the step of dehydrating 2,3-butanediol. As the scandium oxide, commercially available products may be used, and the scandium oxide may also be prepared from nitrate, carbonate or the like of scandium. The amount of the scandium oxide catalyst is not limited, and may be set appropriately. The amount is usually not less than 0.01 g, preferably not less than 0.05 g per feed rate of 2,3-butanediol of 1 g/hour. There is no upper limit of the amount of the scandium oxide catalyst, bur, from the viewpoint of the cost, the amount is usually not more than 10 g per feed rate of 2,3-butanediol of 1 g/hour.

The reaction temperature during the step of dehydrating 2,3-butanediol in the presence of scandium oxide of the present invention is preferably not less than 270° C. for maintaining high conversion, and preferably not more than 420° C. for maintaining high selectivity of 1,3-butadiene and/or 3-buten-2-ol. In the temperature range of not less than 270° C. and not more than 420° C., the lower the reaction temperature is, the higher the selectivity of 3-buten-2-ol is; the higher the reaction temperature is, the higher the selectivity of 1,3-butadiene is; and the mixture thereof are produced at an intermediate temperature between these temperatures. In the Examples below (the cases where scandium oxide prepared at a calcination temperature of 800° C. were used), when the reaction temperature is not more than 350° C., the selectivity of 1,3-butadiene is less than 10%, and 3-buten-2-ol is mainly produced; whereas when the reaction temperature is not less than 400° C., the selectivity of 1,3-butadiene is not less than 74%, and 1,3-butadiene is mainly produced. Therefore, by selecting the reaction temperature properly, it is possible to select whether 1,3-butadiene is mainly produced, 3-buten-2-ol is mainly produced, or the mixture thereof is produced. As described below, since the acid catalyst can be provided at downstream side part in the catalyst layer to dehydrate the produced 3-buten-2-ol to produce 1,3-butadiene, this method can also produce 1,3-butadiene mainly through one step operation.

The scandium oxide to be used in the present invention is preferably one prepared by calcination. The calcination temperature is preferably not less than 500° C. and not more than 1000° C., particularly preferably not less than 700° C.

and not more than 1000° C. The calcination of scandium oxide may be carried out with an electric furnace or the like by heating the scandium oxide while flowing an oxygen-containing gas inside the furnace. The flow rate of the oxygen-containing gas and the calcination time may be adjusted properly. For example, when the electric furnace having an internal volume of 2 L is used, the calcination can be carried out while flowing air at a flow rate of about 10 to 60 mL/min. for about 1 hour to 12 hours, but the calcination condition is not limited thereto.

The present invention may comprise the step of dehydrating 3-buten-2-ol produced in the step of dehydrating 2,3-butanediol in the presence of the above-described scandium oxide, in the presence of an acid catalyst to produce 1,3-butadiene. Although the amount of the acid catalyst to be used is not limited and may be set properly, it is usually not less than 0.01 g, preferably not less than 0.05 g with respect to the feed rate of 1 g/hour of 3-buten-2-ol. Although the upper limit of the amount of the acid catalyst to be used is not limited, it is usually not more than 10 g with respect to the feed rate of 1 g/hour of 3-buten-2-ol.

The dehydration step of 3-buten-2-ol may be allowed to proceed in the same reaction tube as that used in the dehydration step of 2,3-butanediol. In this case, by packing the catalyst to be used in the dehydration of 2,3-butanediol at the upstream side of the flow pass of the raw material, and by packing the catalyst to be used in the dehydration of 3-buten-2-ol at the downstream side thereof, the dehydration of 2,3-butanediol and the dehydration of 3-buten-2-ol may be allowed to proceed sequentially to produce 1,3-butadiene.

The dehydration of 2,3-butanediol and the dehydration of 3-buten-2-ol may also be allowed to proceed with separate reactor. In this case, 3-buten-2-ol produced in the step of dehydrating 2,3-butanediol may be a purified one or a crude one.

The acid catalyst used in the step of dehydrating 3-buten-2-ol is not limited, and a solid acid commonly used in gas phase dehydration reaction may be used. Examples of the acid catalyst include alumina, silica, silica-alumina, titania, zeolite, diatomaceous earth, clay, phosphoric acid and alkali metal phosphate.

The 3-buten-2-ol obtained by dehydrating 2,3-butanediol exists as liquid at ordinary temperature and atmospheric pressure and may be recovered as a liquid component among products of the dehydration reaction. The recovered 3-buten-2-ol may be separated from the other components, for example, by distillation. When the 3-buten-2-ol was obtained as a mixture with water, the 3-buten-2-ol and water are separated by azeotropic distillation, separation membrane such as zeolite membrane, or the like to obtain 3-buten-2-ol with high purity.

The 1,3-butadiene produced by the dehydration of 2,3-butanediol or the dehydration of 3-buten-2-ol may be purified by distillation, extractive distillation or the like.

In cases where the conversion is less than 100% in the dehydration of 2,3-butanediol, unreacted 2,3-butanediol may be recovered as a liquid component. The recovered 2,3-butanediol may be separated from the other components, for example, by distillation. The separated 2,3-butanediol may be reused to increase the yield of 1,3-butadiene and/or 3-buten-2-ol.

EXAMPLE

The present invention will now be explained by way of Examples, but the present invention is not limited to the Examples below.

The conversion and the selectivity shown in the Examples below were calculated according to the following calculation equations (Equation 1) and (Equation 2) respectively.

Conversion (%)=((amount of feed raw material−amount of raw material after reaction)/amount of feed raw material))×100    (Equation 1)

Yield (%)=(amount of product)/(amount of feed raw material)×100    (Equation 2)

In Examples and Comparative Examples, the fixed-bed flow-type reactor shown in FIG. 1 was used. The reactor comprising a quartz reaction tube 4 having an inner diameter of 20 mm and a total length of 400 mm, a vaporizer 3 having a carrier-gas inlet 2 and a raw material inlet 1 in an upper portion of the reaction tube, and a reaction liquid collection container (condenser) 7 having a gas vent 8 in the bottom end was used. The catalyst was fixed and packed in the central portion of the reaction tube, and the catalyst layer 6 was heated to the reaction temperature with a ceramics electric tubular furnace 5 (ASAHIRIKA SEISAKUSHO, ARF-30KC, inner length of the furnace: 300 mm), followed by keeping the temperature. During the reaction, the reaction liquid collection container 7 was cooled in an ice bath.

The reaction was continued for 3 hours or 5 hours. At hourly intervals, the collected reaction solution and gas leaked form the gas vent were subjected to gas chromatography analysis. A calibration curve prepared by using the standard sample of each compound and the peak area value of each compound were used to calculate the content of each compound, and the conversion of the raw material and the selectivity of the product were determined. For the conversion and selectivity based on the entire reaction time, the averages of the conversion and selectivity determined at hourly intervals were calculated.

Reference Example 1

Calcination of Scandium Oxide

Scandium oxide ($Sc_2O_3$, Kanto Chemical Co., Inc.) was left to stand in an electric furnace (internal volume: 2 L) through which air is allowed to flow (flow rate: 30 mL/min.) and heated to calcination temperatures (600° C., 700° C., 800° C., 900° C. or 1000° C.) at a rate of 100° C./h, followed by keeping the calcination temperatures for 3 hours to carry out calcination.

Examples 1 to 8

Dehydration Reaction of 2,3-Butanediol

The scandium oxide (1.0 g) calcined at 800° C. was packed in a reaction tube, and hydrogen was allowed to flow at a flow rate of 45 mL/min. from a carrier-gas inlet. The reaction temperatures were as shown in Table 1. 2,3-Butanediol (Tokyo Chemical Industry Co., Ltd., a mixture of steric isomers) was fed to the vaporizer from the raw material inlet at a flow rate of 1.06 g/hour with a syringe pump and introduced to the reaction tube together with the carrier gas. The reaction was continued for 5 hours. The averages of the conversion and selectivity for 5 hours were shown in Table 1.

TABLE 1

|  | Reaction Temperature (° C.) | Conversion (mol %) | Selectivity (mol %) | | | | |
| --- | --- | --- | --- | --- | --- | --- | --- |
|  |  |  | MEK | 3B2O | 13BD | Others | 3B2O + 13BD |
| Example 1 | 275 | 19.5 | 1.63 | 89.8 | 0.00 | 8.52 | 89.8 |
| Example 2 | 300 | 47.9 | 3.15 | 86.0 | 0.00 | 10.8 | 86.0 |
| Example 3 | 325 | 99.9 | 2.01 | 87.1 | 3.50 | 7.36 | 90.6 |
| Example 4 | 350 | 99.8 | 3.32 | 76.6 | 7.62 | 12.4 | 84.3 |
| Example 5 | 375 | 100 | 4.23 | 52.0 | 31.8 | 12.0 | 83.8 |
| Example 6 | 400 | 100 | 3.36 | 10.7 | 74.5 | 11.4 | 85.3 |
| Example 7 | 411 | 100 | 0.90 | 0.88 | 90.4 | 7.85 | 91.3 |
| Example 8 | 425 | 100 | 11.0 | 2.30 | 63.3 | 23.4 | 65.6 |

MEK = Methyl ethyl ketone,
3B2O = 3-Buten-2-ol,
13BD = 1,3-Butadiene

Examples 9 to 11

Dehydration Reaction of 2,3-Butanediol

Dehydration reactions were carried out in the same manner as in Example 1 except that nitrogen was used as a carrier gas, the reaction temperatures shown in Table 2 were used and the reaction time was 3 hours. The averages of the conversion and selectivity for 3 hours were shown in Table 2.

TABLE 2

|  | Reaction Temperature (° C.) | Conversion (mol %) | Selectivity (mol %) | | | | |
| --- | --- | --- | --- | --- | --- | --- | --- |
|  |  |  | MEK | 3B2O | 13BD | Others | 3B2O + 13BD |
| Example 9 | 325 | 97.3 | 6.50 | 74.4 | 6.94 | 12.2 | 81.3 |
| Example 10 | 375 | 100.0 | 4.23 | 49.4 | 34.3 | 12.1 | 83.7 |
| Example 11 | 411 | 100.0 | 4.94 | 2.84 | 78.7 | 13.5 | 81.5 |

MEK = Methyl ethyl ketone,
3B2O = 3-Buten-2-ol,
13BD = 1,3-Butadiene

Examples 12 to 21

Dehydration Reaction of 2,3-Butanediol

Dehydration reactions were carried out in the same manner as in Example 1 except that scandium oxide calcined at the temperatures shown in Table 3, and the reaction temperatures shown in Table 3 were used. The averages of the conversion and selectivity for 5 hours were shown in Table 3.

TABLE 3

|  | Calcination Temperature (° C.) | Reaction Temperature (° C.) | Conversion (mol %) | Selectivity (mol %) | | | | |
| --- | --- | --- | --- | --- | --- | --- | --- | --- |
|  |  |  |  | MEK | 3B2O | 13BD | Others | 3B2O + 13BD |
| Example 12 | 1000 | 325 | 96.4 | 3.66 | 88.4 | 1.17 | 6.76 | 89.6 |
| Example 13 | 900 | 325 | 97.3 | 3.26 | 87.5 | 1.35 | 7.90 | 88.8 |
| Example 3 | 800 | 325 | 99.9 | 2.01 | 87.1 | 3.50 | 7.36 | 90.6 |
| Example 14 | 700 | 325 | 98.1 | 3.32 | 86.0 | 1.30 | 9.35 | 87.3 |
| Example 15 | 600 | 325 | 99.3 | 3.94 | 81.2 | 2.10 | 12.8 | 83.3 |
| Example 16 | Not calcined | 325 | 74.9 | 7.99 | 60.1 | 0.00 | 31.9 | 60.1 |
| Example 17 | 1000 | 411 | 100 | 6.61 | 3.12 | 68.2 | 22.1 | 71.3 |
| Example 18 | 900 | 411 | 100 | 12.0 | 2.10 | 64.2 | 21.7 | 66.3 |
| Example 7 | 800 | 411 | 100 | 0.90 | 0.88 | 90.4 | 7.85 | 91.3 |
| Example 19 | 700 | 411 | 100 | 1.79 | 1.24 | 85.2 | 11.8 | 86.5 |

TABLE 3-continued

| | Calcination Temperature (° C.) | Reaction Temperature (° C.) | Conversion (mol %) | Selectivity (mol %) | | | | 3B2O + 13BD |
|---|---|---|---|---|---|---|---|---|
| | | | | MEK | 3B2O | 13BD | Others | |
| Example 20 | 600 | 411 | 100 | 7.07 | 0.99 | 71.4 | 20.5 | 72.4 |
| Example 21 | Not calcined | 411 | 100 | 10.4 | 5.54 | 55.7 | 28.4 | 61.2 |

MEK = Methyl ethyl ketone,
3B2O = 3-Buten-2-ol,
13BD = 1,3-Butadiene

Comparative Example 1

Dehydration Reaction of 2,3-Butanediol

In accordance with Patent Document 2, cesium oxide-silica complex was prepared by the following procedure. Cesium carbonate (Wako Pure Chemical Industries, Ltd., 4.65 g) was dissolved in ultrapure water (50 mL), and silica gel (Sigma-Aldrich, Davisil (registered trademark), 35-60 mesh, 10 g) was added to the resulting solution. The obtained mixture was stirred at 80° C. for 24 hours to evaporate water. The obtained powder was calcined under air flow at 600° C., to prepare cesium oxide-silica complex (13.1 g).

The cesium oxide-silica complex (5.0 g) was packed in a reaction tube, and nitrogen was allowed to flow from the carrier-gas inlet at a flow rate of 45 mL/min. The reaction temperature was 400° C. 2,3-Butanediol (Tokyo Chemical Industry Co., Ltd., a mixture of steric isomers) was fed to the vaporizer from the raw material inlet at a flow rate of 2 mL/hour with a syringe pump and introduced to the reaction tube together with the carrier gas. The reaction was continued for 5 hours. The averages of the conversion and selectivity for 5 hours were shown in Table 4.

Comparative Examples 2 to 16

Dehydration Reaction of 2,3-Butanediol

Dehydration reactions were carried out in the same manner as in Example 1 except that the metal oxides shown in Table 4 were used as a catalyst instead of scandium oxide, and the reaction temperatures shown in Table 4 were used. The metal oxides prepared by calcination at 800° C. using a method described in Reference Example 1 were used. The averages of the conversion and selectivity for 5 hours were shown in Table 4.

Comparative Example 17

Dehydration of 2,3-Butanediol

Reaction was carried out in the same manner as in Example 1 except that alumina (Catalysis Society of Japan, Reference catalyst of Catalysis Society of Japan, JRC-ALO-6) was used, and the reaction temperature was 350° C. The averages of the conversion and selectivity for 5 hours were shown in Table 4.

TABLE 4

| | Catalyst | Reaction Temperature (° C.) | Conversion (mol %) | Selectivity (mol %) | | | | 3B2O + 13BD |
|---|---|---|---|---|---|---|---|---|
| | | | | MEK | 3B2O | 13BD | Others | |
| Comparative Example 1 | Cesium oxide-silica complex | 400 | 86.4 | 7.60 | 23.9 | 18.4 | 50.1 | 42.3 |
| Comparative Example 2 | Yttrium oxide ($Y_2O_3$) | 325 | 8.91 | 3.64 | 14.4 | 0.00 | 81.9 | 14.4 |
| Comparative Example 3 | Lanthanum oxide ($La_2O_3$) | 325 | 5.37 | 9.70 | 9.45 | 0.00 | 80.9 | 9.45 |
| Comparative Example 4 | Cerium oxide ($CeO_2$) | 325 | 36.2 | 41.3 | 2.05 | 0.14 | 56.5 | 2.19 |
| Comparative Example 5 | Praseodymium oxide ($Pr_6O_{11}$) | 325 | 5.96 | 8.62 | 2.70 | 0.00 | 88.7 | 2.70 |
| Comparative Example 6 | Samarium oxide ($Sm_2O_3$) | 325 | 6.69 | 3.86 | 11.0 | 0.00 | 85.2 | 11.0 |
| Comparative Example 7 | Europium oxide ($Eu_2O_3$) | 325 | 8.65 | 5.69 | 8.12 | 0.00 | 86.2 | 8.12 |
| Comparative Example 8 | Gadolinium oxide ($Gd_2O_3$) | 325 | 8.11 | 6.03 | 23.1 | 0.00 | 70.9 | 23.1 |
| Comparative Example 9 | Terbium oxide ($Tb_4O_7$) | 325 | 7.27 | 4.52 | 7.83 | 0.00 | 87.7 | 7.83 |
| Comparative Example 10 | Dysprosium oxide ($Dy_2O_3$) | 325 | 9.86 | 4.58 | 33.9 | 0.00 | 61.5 | 33.9 |
| Comparative Example 11 | Dysprosium oxide ($Dy_2O_3$) | 425 | 99.1 | 29.8 | 18.3 | 0.65 | 51.3 | 18.9 |
| Comparative Example 12 | Holmium oxide ($Ho_2O_3$) | 325 | 5.92 | 21.6 | 7.03 | 0.00 | 71.4 | 7.03 |
| Comparative Example 13 | Erbium oxide ($Er_2O_3$) | 325 | 11.2 | 3.10 | 26.9 | 0.05 | 70.0 | 26.9 |

TABLE 4-continued

| | Catalyst | Reaction Temperature (° C.) | Conversion (mol %) | Selectivity (mol %) | | | | |
|---|---|---|---|---|---|---|---|---|
| | | | | MEK | 3B2O | 13BD | Others | 3B2O + 13BD |
| Comparative Example 14 | Thulium oxide ($Tm_2O_3$) | 325 | 1.41 | 8.56 | 0.00 | 0.00 | 91.4 | 0.00 |
| Comparative Example 15 | Ytterbium oxide ($Yb_2O_3$) | 325 | 16.0 | 2.01 | 44.8 | 0.00 | 53.2 | 44.8 |
| Comparative Example 16 | Ytterbium oxide ($Yb_2O_3$) | 425 | 97.3 | 2.74 | 8.50 | 28.3 | 60.5 | 36.8 |
| Comparative Example 17 | Alumina ($Al_2O_3$) | 350 | 100 | 34.0 | 0.36 | 40.4 | 25.3 | 40.7 |

MEK = Methyl ethyl ketone,
3B2O = 3-Buten-2-ol,
13BD = 1,3-Butadiene

Example 22

Dehydration Reaction of 3-Buten-2-ol

Dehydration reaction was carried out in the same manner as in Example 1 except that 3-buten-2-ol (Sigma-Aldrich) was used as a raw material, alumina (Catalysis Society of Japan, Reference catalyst of Catalysis Society of Japan, JRC-ALO-6) was used as a catalyst, and the reaction temperature was 350° C. The averages of the conversion and selectivity for 5 hours were as follows:
Conversion (mol %): 100
Selectivity of 1,3-butadiene (mol %): 94.9

Example 23

Dehydration Reaction of 2,3-Butanediol and 3-buten-2-ol

Reaction was carried out in the same manner as in Example 1 except that, as a catalyst, scandium oxide (1.0 g) calcined at 800° C. was packed on the top of the catalyst layer, and alumina (Catalysis Society of Japan, Reference catalyst of Catalysis Society of Japan, JRC-ALO-6, 1.0 g) was packed at the lower part; the reaction temperature was 318° C., and the flow rate of hydrogen was 80 mL/min. The averages of the conversion and selectivity for 5 hours were as follows:
Conversion (mol %): 100
Selectivity of 1,3-butadiene (mol %): 94.2

Reference Example 2

Recovery of 2,3-Butanediol

Pseudo-reaction solution was prepared in conformity with the composition of the reaction solution generated in Example 1. That is, 2,3-butanediol (Tokyo Chemical Industry Co., Ltd., a mixture of steric isomers, 97%, 46.45 g), methyl ethyl ketone (Kanto Chemical Co., Inc., 99%, 144 mg), iso-butylaldehyde (Tokyo Chemical Industry Co., Ltd., 97%, 219 mg), iso-butanol (Kanto Chemical Co., Inc., 99%, 81 mg), 3-buten-2-ol (Sigma-Aldrich, 97%, 8.09 g) and distillation water (2.18 g) were mixed to prepare the pseudo-reaction solution. The obtained pseudo-reaction solution was distilled under reduced pressure to separate 2,3-butanediol (44.96 g). The purity of the separated 2,3-butanediol that was measured by gas chromatography was 98.2%. The recovery rate of 2,3-butanediol was 98%.

Examples 1 to 21 showed that 1,3-butadiene and/or 3-buten-2-ol could be produced with high selectivity by dehydrating 2,3-butanediol in the presence of scandium oxide.

Examples 12 to 21 showed that the selectivity of 1,3-butadiene and/or 3-buten-2-ol tended to be increased by calcining scandium oxide.

Examples 1 to 21 and Comparative Example 1 showed that the method using scandium oxide could provide higher selectivity of 1,3-butadiene and/or 3-buten-2-ol compared with the prior art using the cesium oxide-silica complex.

Comparative Examples 2 to 16 showed that most of the catalysts which dehydrate 4-methyl-2-pentanol to produce 4-methyl-1-pentene selectively as disclosed in Non-patent Document 9 could not apply to the dehydration of 2,3-butanediol to produce 3-buten-2-ol.

Comparative Example 17 showed that in the case of the common acid catalyst alumina, a large amount of methyl ethyl ketone was produced by dehydrating 2,3-butanediol, and the selectivity of 1,3-butadiene and/or 3-buten-2-ol was low.

Example 22 showed that 1,3-butadiene could be produced with high selectivity by dehydrating 3-buten-2-ol in the presence of an acid catalyst.

Example 23 showed that 1,3-butadiene could be produced with high selectivity by dehydrating 2,3-butanediol in the presence of scandium oxide in the first step and dehydrating 3-buten-2-ol produced in the first step, in the presence of an acid catalyst in the second step.

Reference Example 2 showed that the unreacted 2,3-butanediol in the dehydration reaction of 2,3-butanediol could be recovered with high recovery rate and high purity by distillation of the reaction solution.

INDUSTRIAL AVAILABILITY

By the present invention, 1,3-butadiene and/or 3-buten-2-ol can be produced with high selectivity from 2,3-butanediol without using a radioactive substance. The present invention is industrially extremely useful since 1,3-butadiene is a key chemical product which can be a raw material for synthetic rubbers and nylon, and 3-buten-2-ol can be converted easily to 1,3-butadiene and can be a raw material for pharmaceuticals and the like.

DESCRIPTION OF SYMBOLS

1 Raw material inlet
2 Carrier-gas inlet

3 Vaporizer
4 Reaction tube
5 Tubular furnace
6 Catalyst layer
7 Reaction liquid collection container (Condenser)
8 Gas vent

The invention claimed is:

1. A method for producing 1,3-butadiene and/or 3-buten-2-ol, said method comprising the step of dehydrating 2,3-butanediol in the presence of scandium oxide.

2. The method according to claim 1, wherein the reaction temperature of the step of dehydrating 2,3-butanediol is not less than 270° C. and not more than 420° C.

3. The method according to claim 1, wherein the scandium oxide is one prepared by calcination at a temperature range of not less than 500° C. and not more than 1000° C.

4. The method according to claim 1, further comprising the step of dehydrating 3-buten-2-ol produced in the step of dehydrating 2,3-butanediol, in the presence of an acid catalyst to produce 1,3-butadiene.

* * * * *

UNITED STATES PATENT AND TRADEMARK OFFICE
CERTIFICATE OF CORRECTION

| | | |
|---|---|---|
| PATENT NO. | : 9,452,963 B2 | Page 1 of 1 |
| APPLICATION NO. | : 14/917779 | |
| DATED | : September 27, 2016 | |
| INVENTOR(S) | : Satoshi Sakami et al. | |

It is certified that error appears in the above-identified patent and that said Letters Patent is hereby corrected as shown below:

On the Title Page

At item (73) Assignee should read: -- Toray Industries, Inc., Tokyo, JP; National University Corporation Chiba University, Chiba, JP --

Signed and Sealed this
Fifth Day of February, 2019

Andrei Iancu
*Director of the United States Patent and Trademark Office*